United States Patent [19]

Jones et al.

[11] Patent Number: 4,826,961
[45] Date of Patent: May 2, 1989

[54] METHOD FOR PREPARING RADIOPHARMACEUTICAL COMPLEXES

[75] Inventors: Alun G. Jones, Newton Centre; Alan Davison, Needham, both of Mass.; Michael J. Abrams, Westchester, Pa.

[73] Assignees: President and Fellows of Harvard College; Massachusetts Institute of Technology, both of Cambridge, Mass.

[21] Appl. No.: 6,562

[22] Filed: Jan. 22, 1987

Related U.S. Application Data

[62] Division of Ser. No. 675,540, Nov. 28, 1984, Pat. No. 4,707,544.

[51] Int. Cl.$^4$ ................ C07F 13/00; A61K 49/00
[52] U.S. Cl. ................................. 534/14; 424/1.1; 252/644; 252/645
[58] Field of Search ............. 424/1.1, 9; 534/10, 534/14; 252/645, 644

[56] References Cited

U.S. PATENT DOCUMENTS

| | | | |
|---|---|---|---|
| 4,001,583 | 1/1977 | Barrett | 424/1.1 X |
| 4,256,725 | 3/1981 | Rutner et al. | 436/810 X |
| 4,452,774 | 6/1984 | Jones et al. | 424/1.1 |
| 4,481,184 | 11/1984 | Kronauge et al. | 424/1.1 |

OTHER PUBLICATIONS

Wistow et al., J. Nucl. Med., vol. 19, 483–487 (1979).
Smith et al., J. Nucl. Med., vol. 17, 126–132 (1976).
Deutsch et al., Science, vol. 214, 85–86 (1981).
Kassis, A. I., et al., J. Nucl. Med. vol. 21, 88–90 (1980).
Millar, A. M., Nuclear Med. Comm, 5, 195–199 (1984).
Davison et al., Inorg. Chem. 20 (No. 6): 1629–1632 (1981).
Jones et al., J. Nuclear Med. 21 (No. 3): 279–281 (1980).
Treichel et al., Inorg. Chem. 16 (No. 5): 1167–1169 (1977).
Wistow, Brian W. et al., Clinical Sciences, The Journal of Nuclear Medicine, vol. 19 (No. 5): 483–487 (1978).
Szalda, David J. et al., Inorganic Chemistry, 21: 3851–3857 (1981).
Mialki, William S., et al., Inorganic Chemistry, 20: 480–485 (1982).
Doonan, Daniel J., et al., Inorganic Chemistry, vol. 13 (No. 4) (1974); pp. 921–927.
Duetsch, Edward et al., The Journal of Nuclear Medicine, 22: 897–907 (1981).

*Primary Examiner*—John S. Maples
*Attorney, Agent, or Firm*—Sewall P. Bronstein; George W. Neuner

[57] ABSTRACT

A method for preparing radiopharmaceutical complexes that are substantially free of the reaction materials used to produce the radiopharmaceutical complex is disclosed. The method involves admixing in a suitable first solvent in a container a target seeking ligand or salt or metal adduct thereof, a radionuclide label, and a reducing agent for said radionuclide, thereby forming said radiopharmaceutical complex; coating the interior walls of the container with said pharmaceutical complex; discarding the solvent containing by-products and unreacted starting reaction materials; and removing the radiopharmaceutical complex from said walls by dissolving it in a second solvent, thereby obtaining said radiopharmaceutical complex substantially free of by-products and unreacted starting materials.

6 Claims, No Drawings

METHOD FOR PREPARING RADIOPHARMACEUTICAL COMPLEXES

This invention was made with Government support and the U.S. Government has certain rights in the invention.

This is a divisional of application Ser. No. 675,540 filed on Nov. 28, 1984, now U.S. Pat. No. 4,707,544.

FIELD OF THE INVENTION

This invention relates to novel isonitrile complexes of radionuclides, i.e., for example, of radioactive isotopes such as, but not limited to, $^{99m}$Tc, $^{99}$Tc, $^{97}$Ru, $^{51}$Cr, $^{57}$Co, $^{188}$Re, and $^{191}$Os, and particularly to metal-isonitrile adducts of making such radionuclide complexes wherein the metal adduct comprises Zn, Ga, Cd, In, Sn, Hg, Tl, Pb or Bi.

BACKGROUND OF THE INVENTION

A variety of radioisotope imaging and labelling agents have been developed in the past; however, the materials previously available have generally suffered from the shortcomings of high cost, complexity of the method of preparation, or failure to exhibit high quality imaging or highly effective labelling.

Isonitrile complexes of various non radioactive metals have been described but there has been no suggestion that isonitrile complexes of radionuclides would have properties making them desirable or useful as imaging or labelling agents. Oxine complexes of $^{99m}$Tc have been described for use in labelling platelets. Wistow et al., *J. Nucl. Med.*, Vol. 19, 483–487 (1978). The direct labelling of red blood cells with $^{99m}$Tc by a reductive process, and the use of the labelled cells for imaging have been described. Smith et al., *J. Nucl. Med.*, Vol. 17, -132 (1976). Various complexes of $^{99m}$Tc with arsenic- and phosphorus-containing organic compounds have been proposed for use as imaging and labelling agents. Deutsch et al., *Science*, Vol 214, 85–86 (1981); *J. Nucl. Med.*, Vol. 22, 897–907 (1981); European Pat. Appln. No. 81400618.5, published Oct. 28, 1981, Publn. No. 0038756.

U.S. Pat. No. 4,452,774 describes a coordination complex of an isonitrile ligand with a radioactive metal (radionuclide) selected from the class consisting of radioactive isotopes of Tc, Ru, Co, Pt, Fe, Os, Ir, W, Re, Cr, Mo, Mn, Ni, Rh, Pd, Nb, and Ta, and methods for using such complexes. Preferably, the isonitrile complexes comprise one of the above radioactive metals wherein each available coordination site is filled with an isonitrile ligand. The isonitrile ligand can be either monodentate or polydentate such as, for example, bidentate or tridentate. Also described is a kit comprising an isonitrile ligand and a reducing agent capable of reducing the radioactive metal to form the coordination complex.

Because of the general availability of supplies of $^{99m}$Tc in clinical laboratories in the form of pertechnetate as well as the desirable half-life and gamma ray energy of this radionuclide, the complexes preferably contain $^{99m}$Tc, although complexes with other radionuclides are also described. Moreover, the general availability of supplies of pertechnetate make it convenient to use kits for preparation of various complexes of $^{99m}$Tc.

The isonitrile complexes can readily be prepared and isolated at both macro and tracer concentrations in aqueous media, together with any of a wide variety of counterions, as appropriate. They display remarkably effective labelling characteristics for liposomes or vesicles, and a variety of living cells containing lipid membranes, and are also effective imaging agents for detecting abnormalities in the tissues of various organs, particularaly in the heart, as well as the existence of blood clots. The complexes of $^{99m}$Tc are particularly preferred because of the desirable nuclear properties of this radioisotope, i.e., its half-life and gamma ray energy.

One problem encountered in preparing the isonitrile complexes described in U.S. Pat. No. 4,452,774 is that many isonitrile ligands are extremely volatile. Thus, the isonitrile ligand is difficult to handle and lyophilized kits are not practical. Therefore, new and better ways for handling the isonitrile ligands for making radionuclide complexes are being sought.

SUMMARY OF THE INVENTION

We have found that some of the above problems can be overcome by preparing soluble metal-salt adducts of the isonitrile ligands and using the metal-isonitrile adduct to prepare the desired radionuclide complex for radiolabelling. Surprisingly, we were not able to form the sodium or calcium salt adduct of the isonitriles. In addition, other metals that do form adducts of the isonitriles such as manganese, iron, rhenium and ruthenium have not been successfully displaced from their isonitrile adducts (or salts) by, for instance, technetium to form the desired radionuclide complex with the isonitrile.

Therefore, the present invention provides a method for preparing a radionuclide coordination complex of an isonitrile ligand and a radioactive metal selected from the class consisting of radioactive isotopes of Tc, Ru, Co, Pt, Fe, Os, Ir, W, Re, Cr, Mo, Mn, Ni, Rh, Pd, Nb and Ta, said method comprising forming a soluble metal adduct of said isonitrile ligand by admixing said ligand with a salt of a displaceable metal having a complete d-electron shell selected from the class consisting of Zn, Ga, Cd, In, Sn, Hg, Tl, Pb and Bi to form a soluble metal-isonitrile salt, and admixing said metal-isonitrile salt with said radioactive metal in a suitable solvent to displace said displaceable metal with the radioactive metal.

In another embodiment of this invention, a method is provided for preparing radiopharmaceutical complexes that are substantially free of the reaction materials used to produce the radiopharmaceutical complex. The method comprises forming the radiopharmaceutical complex by admixing in a suitable solvent in a container a target-seeking ligand or salt or metal adduct thereof, a radionuclide label such as, for instance, technetium-99m and a reducing agent, if required, to form the radiopharmaceutical complex; coating the interior walls of the container with the radiopharmaceutical complex; discarding the solvent containing non-complexed ligand and radionuclide, non-used starting reaction materials and oxidized reducing agent if present; and dissolving the desired radiopharmaceutical complex from the container walls with another solvent to obtain said complex substantially free of starting reaction materials and unwanted reaction by-products. The method can also include one or more rinsing steps to further remove starting reaction materials and unwanted reaction by-products to obtain said complex essentially free of such starting materials and by-products.

DETAILED DESCRIPTION OF THE INVENTION

In accord with the present invention, metals having complete d-electron shells are used to form metal adducts of isonitriles. The metal-isonitrile adducts are then reacted with a radioactive isotope selected from the list above to form the desired radionuclide complex. The metals useful in the practice of this invention are selected from the class consisting of Zn, Ga, Cd, In, Sn, Hg, Tl, Pb and Bi.

Any isonitrile ligand can be used in the practice of this invention. Suitable isonitrile ligands include those having, for example, the formula CNR where the organic radical R can be aliphatic or aromatic and may be substituted with a variety of groups which may or may not be charged. Among the aromatic R groups which may be present are phenyl, tolyl, xylyl, naphtyl, diphenyl and substituted aromatic groups containing such substitutents as halo, e.g., chloro, bromo, iodo or fluoro; hydroxy, nitro, alkyl, alkoxy, etc.; among the aliphatic R groups which may be present are alkyl, preferably containing 1 to 20 carbon atoms, such as methyl, ethyl, n-propyl, isopropyl, n-butyl, isobutyl, n-hexyl, 2-ethylhexyl, dodecyl, stearyl, etc. Substituent groups may also be present in the aliphatic groups, including among others the same substituent groups as those listed above for aromatic groups.

When the isonitrile ligand is a polydentate ligand such as, for example, a bidentate ligand having the structure CNRNC, the organic radical portion of the ligand can be the same as defined for R above.

In general, because the desired lipophilic characteristics in the radionuclide complex can be achieved without the need for substituent groups, it is preferred for the sake of simplicity to employ unsubstituted hydrocarbon groups as the R groups. However, the lipophilic characteristics of the complex can be further varied by varying the R groups to adapt the complex for labelling selected materials, for membrane transport such as for the blood-brain barrier, or for imaging selected organs and dynamic processes related to their function.

The metal-isonitrile adducts of the present invention can readily be prepared by admixing a salt of the displaceable metal and the isonitrile ligand in a suitable media at temperatures from room temperature to reflux temperature or even higher. The reaction is generally complete after about 5 minutes to about 2 hours, depending upon the reagents employed and the conditions used.

Any desired counterion may also be present in the composition, such as chloride, fluoride, bromide, iodide, hydroxide, sulfate or bisulfate, dihydrogen phosphate, fluoroborate, hexafluorophosphate, etc.

The desired labelled radionuclide isonitrile complexes are prepared from the metal-isonitrile adducts by admixing the adduct with a salt of the radioactive metal in suitable media at temperatures from room temperature to reflux temperatures or even higher. The desired labelled isonitrile complexes are isolatable and can be obtained in high yields. In some cases the metal isonitrile adduct can itself act as a reducing agent thus eliminating the need for an additional reducing agent. Additional reducing agents, when required or desired to speed up the reaction, are well known to those skilled in the art. Examples of such well-known reducing agents include stannous salts (often used in the form of kits), formamidine sulfinic acid, sodium dithionite, sodium bisulfite, sodium thiosulfite, hydroxylamine, ascorbic acid, and the like. The reaction is generally complete after about 5 minutes to about 2 hours, depending upon the particular reagents employed and the conditions used. The yield of labelled radionuclide isonitrile complex is preferably at least 70%, and more preferably at least 90% of the radioactive nuclide used for labelling.

In the case of technetium such as, for example $^{99}$Tc or $^{99m}$Tc, an isonitrile complex is preferably made by mixing pertechnetate (Tc$^{VII}$) with an appropriate reducing agent capable of reducing the technetium in aqueous medium, then adding to the reaction mixture the metal-isonitrile adduct. The presently preferred displaceable metal for use when preparing a technetium-isonitrile complex in accord with the present invention is zinc.

Thus, the isonitrile technetium complexes prepared in accord with this invention can be prepared from preformed technetium complexes having oxidation states for technetium of, for instance, III, IV or V, by treating these preformed complexes with an excess of isonitrile ligands under suitable conditions. For example, the technetium-isonitrile complex can also be prepared by reacting the desired isonitrile ligand with the hexakis-thiourea complex of Tc$^{III}$ or with a technetium-glucoheptonate complex, or the like.

An excess of the isonitrile ligand, up to 50 to 100% molar excess or more, and an excess of reducing agent, can be used in the complexing reaction to ensure maximum yield from the technetium. Following the reaction, the desired complex can be separated from the reaction mixture, if required, for example, by crystallization or precipitation or by conventional chromatography or ion exchange chromatography. See U.S. Pat. No. 4,452,774, supra, the disclosure of which is hereby incorporated by reference.

Kits in accord with the present invention comprise an adduct of a displaceable metal (as listed above) and an isonitrile ligand and, if required, a quantity of a reducing agent for reducing a preselected radionuclide. Preferably, such kits contain a predetermined quantity of a metal isonitrile adduct and a predetermined quantity of a reducing agent capable of reducing a predetermined quantity of the preselected radionuclide. It is also preferred that the isonitrile ligand and reducing agent be lyophilized, when possible, to facilitate storage stability. If lyophilization is not practical, the kits are stored frozen. The metal-isonitrile adduct and reducing agent are preferably contained in sealed, sterilized containers.

In one embodiment of the invention, a kit for use in making the radionuclide complexes in accord with the present invention from a supply of $^{99m}$Tc such as the pertechnetate solution in isotonic saline available in most clinical laboratories includes the desired quantity of a selected isonitrile ligand in the form of a metal-isonitrile adduct to react with a predetermined quantity of pertechnetate, and a predetermined quantity of reducing agent such as, for example, stannous ion in the form of stannous glucoheptanate to reduce the predetermined quantity of pertechnetate to form the desired technetium-isonitrile complex.

The following specific examples are intended to illustrate more fully the nature of the present invention without acting as a limitation upon its scope.

EXAMPLE 1

Prepartion of Zn($^t$BuNC)$_2$Br$_2$

Into a clean, dry 250 ml three-necked round-bottomed flask equipped with a stopcock adapter and two rubber septa, place 2.98 g (13.1 mmol) reagent grade zinc bromide and a magnetic stir-bar. Place the flask under oil-pump vacuum ($\leq 1$ mm Hg) for at least two hours. Release the vacuum to dry inert gas and, with the aid of an oil bubbler, leave the flask under a constant head of inert gas. Introduce into the flask, via a cannula, 100 ml anhydrous diethyl ether. With the aid of a magnetic stirrer, stir the mixture until all the zinc bromide has dissolved to give a clear colorless solution. Continue stirring and slowly add, via a syringe, 2.21 g (3.0 ml, 26.6 mmol) t-butyl ($^t$Bu) isonitrile to give the product as a white precipitate. Stir for an additional 15 minutes. Replace one of the septa with a medium-porosity Schlenk frit and a vented receiving flask. Invert the apparatus and filter the mixtue using positive inert gas pressure. Slurry and rinse the solid product three times with 50 ml aliquots of anhydrous diethyl ether, again using positive inert gas pressure. Dry the product in a vigorous flow of dry inert gas for twenty minutes. Quickly transfer the product to a dry tared storage vial and seal under dry inert gas. Store the product at or below 0° C. Yields of 80–85% are obtained.

Dissolve a small ($\sim 30$ mg) sample in d$_6$-acetone and obtain the $^1$HNMR spectrum. Pure compound has only a single resonance at $\delta 1.50$–1.60. The compound has a melting point in the range 82° to 86° C.

EXAMPLE 2

Preparation of Frozen Zn ($^t$BuNC)$_2$Br$_2$ Solution Kits

Hemostat clamp the outlet tube of transfer pack (150 ml; Fenewal ™ #4R2001, available from Travenol Labs., Inc.). In a closed, dry weighing vessel, weigh out 3.12±0.02 g Zn($^t$BuNC)$_2$Br$_2$. Introduce 3.12 g±0.02g Zn($^t$BuNC)$_2$Br$_2$ into the transfer pack usng a small funnel placed on the neck of the transfer pack. Close the neck of the transfer pack with sampling site coupler (Fenewal ™ #4C2405, available from Travenol Labs., Inc.). Introduce 100 ml of fresh 0.9% "sterile, for injection" saline. Minimize head space in the bag by drawing the gas volume into a syringe. Shake the bag until all of the solid is dissolved. Replace the coupler with a connection to the dispensing syringe. Cap the vent of the dispensing syringe with a septum. Place a 0.22 um Millex GV filter and a needle on the syringe. Flush the syringe assembly with 10 ml of saline solution to remove the air bubbles. Set the syringe to deliver 1 ml. Decrimp the empty, sterile vials and remove the stoppers. Place the vials in a tray and cool them with liquid nitrogen. Dispense 1 ml aliquots into the pre-cooled vials. Inject 1 ml into each tared, closed vial. Weigh the vials to ascertain correct delivery. (Net weight should $= 1.0$ to 1.1 g). Restopper and recrimp each vial. Store the vials in a freezer (below 0° C.).

EXAMPLE 3

Preparation of Tc-99m Tertiary Butyl Isonitrile Complexes (TC-TBI)

Thaw one vial of frozen Zn($^t$BuNC)$_2$Br$_2$ solution (prepared in Example 2). Add $^{99m}$TcO$_4$ generator eluent (75 to 100 mCi i.e. 2700–3700 mBq; $\leq 0.8$ ml) to a Glucoscan ™ kit (available from NEN Division, E.I. duPont de Nemours & Co.). Add 0.8 ml Zn($^t$BuNC)$_2$Br$_2$ solution to the admixture of the generator eluent and a Glucoscan ™ kit. Shake the mixture briefly. Place the vial upright in a boiling water bath so that the water level is between one-half and three-fourths of the way up the side of the vial. Heat the mixture for 15 minutes. Remove the vial and allow it to cool for 15 minutes. Withdraw the liquid contents of the vial, and discard the liquid. (The desired product is coated on the vial walls.) Rinse twice by: (a) adding 10 ml H$_2$O to the vial, slowly, allowing excess pressure to blow back into the syringe, and (b) inverting the vial twice, and withdrawing the liquid and discarding. Add 0.75 ml of EtOH to the vial. Shake thoroughly to rinse the desired product off all the inside surfaces of the vial. Slowly add 2.25 ml of 0.9% saline to the vial. The vial should contain a clear, colorless solution. This solution is essentially free of starting materials and reaction by-product.

The desired Tc-TBI product contains greater than 90% of total activity.

Zinc isonitrile adducts can also be prepared in accord with Example 1 for a wide variety of substituents R as set forth above. Some examples of other aliphatic R groups useful for making zinc isonitrile adducts for use in accord with this invention include methyl, n-propyl, isopropyl and cyclohexyl, as well as n-butyl sec-butyl.

Injection of the technetium labelled t-butyl isonitrile product (Tc-TBI) into animal models followed by conventional imaging procedures showed that vascular emboli can be detected in the lungs as well as in other parts of the vasculature, as described below. Following the detection by gamma camera of unidentified sites of localization in the lung field of apparently normal, healthy dogs, the fact that these represented blood clots was determined. Autologous clots prepared in vitro and labeled with small amount of $^{99m}$Tc-sulfur colloid were introduced into the lung of a dog and their position determined by scanning. A large (several mCi) dose of $^{99m}$Tc-hexakis-(tertiary-butyl-isonitrile) technetium (I), i.e. Tc-TBI, was injected and several of the clots were subsequently visualized. Computer analysis of the data collected showed conclusively that localization was occurring. Furthermore, analysis of the initial perfusion phase in the lung showed areas of deficit in blood flow associated with several of the emboli. Other experiments yielded similar results.

Isonitrile complexes prepared in accord with this invention can also be used to label liposomes; to label mammalian cells such as Chinese hamster V-79 lung fibroblast cells, leukocytes isolated from rabbit blood, and human erythrocytes (red blood cells); to visualize bone marrow; to measure lung function; and for mycardial imaging. For instance, both tertiary-butyl and isopropyl isonitrile products have been used to visualize myocardial tissue by external imaging.

Such cells and liposomes can be readily labeled by incubating the radiolabeled complexes of this invention with such cells or liposomes in a suitable medium and measuring the uptake of radioactivity in accord with the methods described by Kassis, A. I. et al., *J. Nucl. Med.*, Vol. 21, 88–90 (1980). Incorporation of the radioactive complex can be as high as 29 pCi/cell. Studies have shown that the radioactive label can be 90% retained for up to sixteen hours. Autologous leukocytes separated from fresh rabbit blood were labeled with the $^{99m}$Tc complex and subsequently reinjected into the rabbit. The distribution of the radiolabeled cells could be followed by gamma camera. Also liposomes have been labeled by similar techniques and their distribution in mice followed by a gamma camera.

Thus, it can be readily appreciated that complexes prepared in accord with this invention can be used to visualize cardiac tissue, to detect the presence of thrombi in the lung and associated areas of blood perfusion deficits, to study lung function, to study renal excretion, and to image bone marrow and the hepatobiliary system. The complexes are further useful for radioactive tagging of cells and formed elements of blood, other animal cells, plant cells, and small organisms which possess membranous exteriors, e.g., single-cell entities, microbes, etc. In addition, they can be employed to label previously prepared liposomes without the necessity for encapsulation as is the case with many other labelling agents. Finally, these complexes can be employed therapeutically.

The choice of radionuclides will depend on the use. For example, preferred radionuclides for diagnostic imaging are radioactive isotopes of Tc, Ru, Co, Pt, Fe, Os, and Ir; preferred radionuclides for therapeutic uses are radioactive isotopes of W, Re, Fe, and Os; preferred radionuclides for radioactive tagging are Cr, Mo, Co, Tc, Fe, Mn, W, Ru, Ni, Rh, Ir, Pd, Nb, and Ta.

This invention has been described in detail including the preferred embodiments thereof. However, it will be appreciated that those skilled in the art, upon consideration of this disclosure, may make modifications and improvements within the spirit and scope of this invention.

We claim:

1. A method for producing a radiopharmaceutical complex that is substantially free of the starting reaction materials and of reaction by-products, said method comprising admixing in a first solvent in a container a target seeking ligand, or salt or metal salt adduct thereof, a radionuclide label, and a reducing agent for said radionuclide, thereby forming said radiopharmaceutical complex; coating the interior walls of the container with said pharmaceutical complex; discarding the solvent containing by-products and unreacted starting reaction materials from said container; and adding a second solvent to said container to remove the radiopharmaceutical complex from said walls by dissolving said complex in said second solvent, thereby obtaining said radiopharmaceutical complex substantially free of by-products and unreacted starting materials.

2. The method of claim 1 wherein said radionuclide label is Tc-99m.

3. The method of claim 1 further comprising the step of rinsing the coated walls with fresh first solvent to further remove by-products and unreacted starting materials to obtain said radiopharmaceutical complex essentially free of by-products and starting materials.

4. The method of claim 1 wherein said target-seeking ligand is an isonitrile ligand that is present as a metal salt adduct of a displaceable metal selected from the group consisting of Zn, Ga, Cd, In, Sn, Hg, Tl, Pb and Bi.

5. The method of claim 4 wherein said radionuclide label is Tc-99m.

6. The method of claim 5 wherein said displaceable metal is Zn.

* * * * *